(12) United States Patent
Kumar et al.

(10) Patent No.: US 9,447,105 B2
(45) Date of Patent: Sep. 20, 2016

(54) TRIAZINE COMPOUNDS AND A PROCESS FOR PREPARATION THEREOF

(71) Applicant: COUNCIL OF SCIENTIFIC & INDUSTRIAL RESEARCH, New Delhi (IN)

(72) Inventors: Pradeep Kumar, Pune (IN); Anand Harbindu, Pune (IN); Brijesh Sharma, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/763,448

(22) PCT Filed: Jan. 24, 2014

(86) PCT No.: PCT/IN2014/000056
§ 371 (c)(1),
(2) Date: Jul. 24, 2015

(87) PCT Pub. No.: WO2014/115171
PCT Pub. Date: Jul. 31, 2014

(65) Prior Publication Data
US 2015/0353566 A1    Dec. 10, 2015

(30) Foreign Application Priority Data

Jan. 24, 2013 (IN) .......................... 0197/DEL/2013

(51) Int. Cl.
*C07D 487/04* (2006.01)
*A61K 31/53* (2006.01)
*A61P 35/00* (2006.01)

(52) U.S. Cl.
CPC ............ *C07D 487/04* (2013.01); *A61K 31/53* (2013.01)

(58) Field of Classification Search
CPC ............................ C07D 487/04; A61K 31/53
USPC .......................................... 544/183; 514/243
See application file for complete search history.

(56) References Cited

U.S. PATENT DOCUMENTS 6,908,916 B2 *  6/2005  Mastalerz ............. C04B 41/009
                                                            514/218
6,982,265 B1      1/2006  Hunt et al.

2006/0211695 A1   9/2006  Borzilleri et al.
2011/0183983 A1   7/2011  Kim et al.
2012/0077814 A1   3/2012  Wang et al.

FOREIGN PATENT DOCUMENTS

| WO | WO 00/71129 A1 | 11/2000 |
| WO | WO 03/042172 A2 | 5/2003 |
| WO | WO 2006/004636 A2 | 1/2006 |
| WO | WO 2009/117157 A1 | 9/2009 |

OTHER PUBLICATIONS

Patil S.A., et al., "Synthesis of Pyrrolo[2-1-*f*][1,2,4]triazine Congeners of Nucleic Acid Purines via N-amination of 2-Substituted Pyrroles [1]"; J. Heterocyclic Chem. vol. 31, Jul. 1994, pp. 781-786.
Hunt, J.T., et al., "Discovery of the Pyrrolo [2,1-f][1,2,4]triazine Nucleus as a New Kinase Inhibitor Template", Journal of Medicinal Chemistry, vol. 47, No. 16, Jun. 23, 2004.
Borzilleri, R.M., et al. "Design, Synthesis, and Evaluation of Orally Active 4-(2,4-Difluoro-5-(methoxycarbamoyl) phenyl amino)—pyrrolo . . . "; Journal of Medicinal Chemistry, vol. 48, May 17, 2005.
Wrobleski, S.T., et al.: "Synthesis and SAR of new pyrrolo [2,1-f][1,2,4]triazine as potent p38alpha MAP kinase inhibitors"; BioOrganic & Medicinal Chemistry Letters, vol. 18, No. 8, Apr. 15, 2008.
XP002723097—Database Registry [Online] Chemical Abstracts Service, Columbus, Ohio; Nov. 13, 2012.
XP002723098—Database Registry [Online] Chemical Abstracts Service, Columbus, Ohio; Jan. 10, 2010.

* cited by examiner

*Primary Examiner* — Venkataraman Balasubramanian
(74) *Attorney, Agent, or Firm* — DLA Piper LLP (US)

(57) ABSTRACT

The present invention discloses triazine compounds of Formula II and a process to synthesize these compounds. Particularly, the invention provides one pot method to synthesize triazines nucleus, wherein the method comprises amination followed by using Leuckart reaction conditions of pyrrole/indole-2-carboxylates of Formula I to obtain corresponding triazine compounds of Formula II.

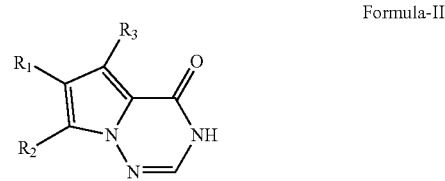

Formula-II

6 Claims, 4 Drawing Sheets

ORTEP Diagram of compound 38

$^1$H NMR (CD$_3$OD, 200 MHz) spectrum of 5,7-dimethylpyrrolo[2,1-*f*][1,2,4]triazin-4(3H)-one $^1$H NMR (CD$_3$OD, 500 MHz) spectrum of pyrrolo[2,1-*f*][1,2,4]triazin-4(3H)-one $^1$H NMR (DMSO-d$_6$, 500 MHz) spectrum of 7-methoxy-[1,2,4]triazino[1,6-a]indol-4(3H)-one $^1$H NMR (CD$_3$OD, 400 MHz) spectrum of 7,8-dimethoxy-[1,2,4]triazino[1,6-a]indol-4(3H)-one $^1$H NMR (DMSO-d$_6$, 400 MHz) spectrum of 6-nitropyrrolo[2,1-f][1,2,4]triazin-4(3H)-one ¹H NMR (CD₃OD, 400 MHz) spectrum of [1,2,4]triazino[1,6-a]indol-4(3H)-one

TRIAZINE COMPOUNDS AND A PROCESS FOR PREPARATION THEREOF

CROSS-REFERENCE TO RELATED APPLICATIONS

This application is a 35 USC §371 National Stage application of International Application No. PCT/IN2014/000056 filed Jan. 24, 2014, now pending; which claims the benefit under 35 USC §119(a) to India Application Serial No. 0197/DEL/2013 filed Jan. 24, 2013. The disclosure of the prior application is considered part of and is incorporated by reference in the disclosure of this application.

FIELD OF THE INVENTION

The present invention relates to triazine compounds and a process for preparation thereof. Particularly, the present invention relates to triazine compounds which are useful for screening of kinases and other related targets. More particularly, the present invention relates to the process for the preparation of novel triazine compounds.

BACKGROUND OF THE INVENTION

In the past decade, researcher's efforts focused at the discovery of therapeutically useful inhibitors of protein kinases have been intensified. These efforts have resulted in the identification of a variety of templates which, depending upon the nature of attached substituents, provide selective inhibition both within and across different protein kinase families. One such effort led to the discovery of pyrrolo[2,1-f][1,2,4]triazine nucleus as a novel kinase inhibitor template which effectively mimics the well-known quinazoline kinase inhibitor scaffold, which has been serving a core template for a variety of ATP-competitive kinase inhibitors.

Thus, the current trend of research is now focused on novel analogs of pyrrolo[2,1-f][1,2,4]triazine so as to provide potent biochemical inhibitors of the tyrosine kinase activity. There is ample literature available on synthesis of novel pyrrolo[2,1-f][1,2,4]triazine molecules.

Aqua mediated one pot facile synthesis of novel thioxo-1,2,4-triazin-5(2h)-one and [1,2,4]triazino[5,6-a]indole derivatives and their biological activities is disclosed by Harshita Sachdeva et al. in J. Chil. Chem. Soc, 57, No 4 (2012), págs: 1348-1354.

WO/2013/177983 (Yang Chunhao et al.) discloses pyrrolo[2,1-f][1,2,4]triazine compounds and their use for treating phosphatidylinositol-3 kinase related diseases such as cancer. EP2289894 (Dyckman Alaric et al.) relates to cycloalkyl, heterocyclo and heteroaryl pyrrolotriazine aniline compounds useful for treating p38 kinase-associated conditions.

Synthesis and antiproliferative activity of [1,2,4]triazino[4,3-a]indoles is reported in anticancer research 24: 3775-3780 (2004) by Paola Barraja et al.

An article titled "Discovery of pyrrolo[2,1-f][1,2,4]triazine C6-ketones as potent, orally active p38a MAP kinase inhibitors" by Dyckman A J, Li T, et al published in Bio. org Med ChemLett. 2011, Aug. 1; 21(15):4633-7 discloses preparation of Pyrrolo[2,1-f][1,2,4]triazine based inhibitors of p38a and explored functional group modifications at the C6 position and concludes that incorporation of aryl and heteroaryl ketones at this position led to potent inhibitors with efficacy in in vivo models of acute and chronic inflammation.

Another article titled "Synthesis and SAR of new pyrrolo [2,1-f][1,2,4]triazines as potent p38 alpha MAP kinase inhibitors" by Wrobleski S T et al published in *Bio. Org. Med. Chem. Lett.* 2008 Apr. 15; 18(8):2739-44, reports a novel series of compounds based on the pyrrolo[2,1-f][1,2,4]triazine ring system have been identified as potent p38 alpha MAP kinase inhibitors.

Yet another article titled "Synthesis of pyrrolo[2,1-f][1,2,4]triazine congeners of nucleic acid purines via the N-amination of 2-substituted pyrroles" by Shirish A. Patil et al published in J. O. Heterocyclic chemistry volume 31, issue 4, pages 781-786, describes synthesis of several new 4-mono- and 2,4-disubstituted pyrrolo[2,1-f][1,2,4]triazines. 1-aminopyrrole-2-carbonitrile intermediates were obtained by N-amination of the corresponding pyrrole-2-carboxaldehyde followed by CHO→CN conversion with either hydroxylamine-O-sulfonic acid or O-mesitylenesulfonylhydroxylamine. Cyclization of the product thus obtained with a variety of amidine reagents or, after conversion of the product to its corresponding amide followed by base-catalyzed annulation completed the synthesis of the title products.

OBJECTS OF THE INVENTION

The main objective of the present invention is to provide triazine compounds and a process for preparation thereof.

Another objective of the present invention is to provide a process for the preparation of novel triazine compounds.

Still another objective of the present invention is to provide triazine compounds which are useful for screening of kinases and other related targets.

SUMMARY OF THE INVENTION

Accordingly, the present invention provides triazine compounds of Formula II,

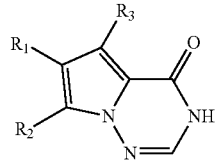

Formula-II wherein, R1, R2, and R3, are independently selected from the group consisting of hydrogen, (C1-C6) alkyl, —NO₂, I, Cl, Br, F, and —CH₂—R7, where R7 is 5 or 6 membered saturated heterocyclic ring, comprising at least one heteroatom selected from the group consisting of N, O, and S which is directly attached to carbon atom of —CH₂; or R1 and R2 together form substituted or unsubstituted aromatic ring as set forth below:

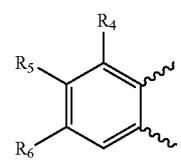

wherein R4, R5, and R6 are individually selected from the group consisting of hydrogen, (C1-C6) alkyl, —NH₂, halogen, —OH, —CN, —NO₂, aryl, alkylaryl, (C1-C8) alkoxy, aryloxy, arylalkoxy, N₃, and R—C≡C—, where R is selected from the group consisting of hydrogen, (C1-C6) alkyl, aryl, alkylaryl.

In one embodiment of the present invention the structural formula of the representative compounds of triazine compounds of Formula II are selected from the group consisting of:

37

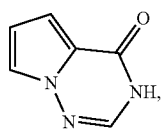

(37)

pyrrolo[2,1-f][1,2,4]triazin-4(3H)-one

38

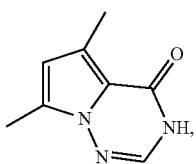

(38)

5,7-dimethylpyrrolo[2,1-f][1,2,4]triazin-4(3H)-one

4

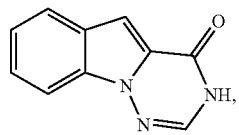

(04)

[1,2,4]triazino[1,6-a]indol-4(3H)-one

41

(41)

7-methoxy-[1,2,4]triazino[1,6-a]indol-4(3H)-one

42

(42)

7-8-dimethoxy-[1,2,4]triazino[1,6-a]indol-4(3H)-one

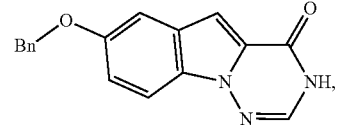

(43)

7-(benzyloxy)-[1,2,4]triazino[1,6-a]indol-4(3H)-one

-continued

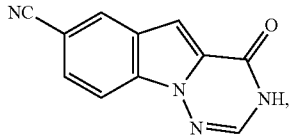

(44)

4-oxo-3,4-dihydro-[1,2,4]triazino[1,6-a]indole-7-carbonitrile

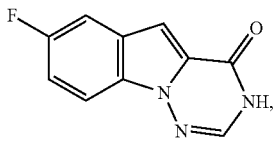

(45)

7-fluoro-[1,2,4]triazino[1,6-a]indol-4(3H)-one

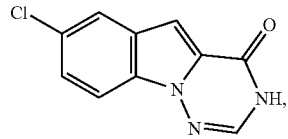

(46)

7-chloro-[1,2,4]triazino[1,6-a]indol-4(3H)-one

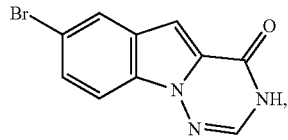

(47)

7-bromo-[1,2,4]triazino[1,6-a]indol-4(3H)-one

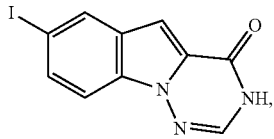

(48)

7-iodo-[1,2,4]triazino[1,6-a]indol-4(3H)-one

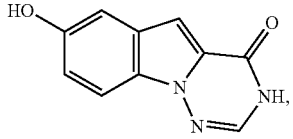

(49)

7-hydroxy-[1,2,4]triazino[1,6-a]indol-4(3H)-one

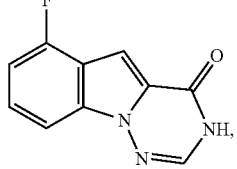

(50)

6-fluoro-[1,2,4]triazino[1,6-a]indol-4(3H)-one

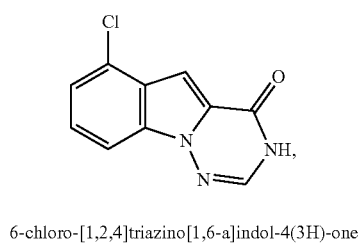

6-chloro-[1,2,4]triazino[1,6-a]indol-4(3H)-one

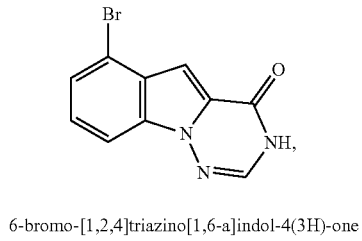

6-bromo-[1,2,4]triazino[1,6-a]indol-4(3H)-one

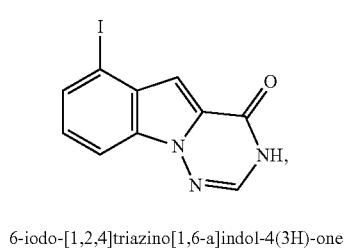

6-iodo-[1,2,4]triazino[1,6-a]indol-4(3H)-one

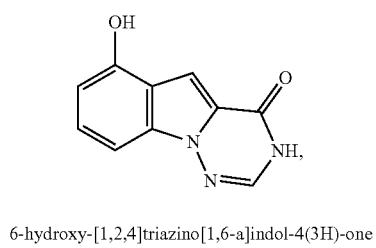

6-hydroxy-[1,2,4]triazino[1,6-a]indol-4(3H)-one

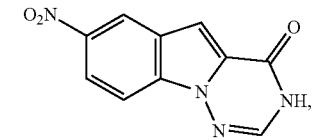

7-nitro-[1,2,4]triazino[1,6-a]indol-4(3H)-one

5-(morpholinomethyl)-[1,2,4]triazino[1,6-a]indol-4(3H)-one

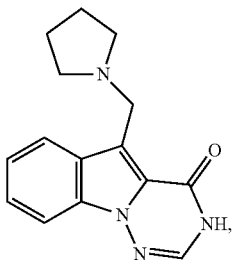

5-(pyrrolidin-1-ylmethyl)-[1,2,4]triazino[1,6-a]indol-4(3H)-one

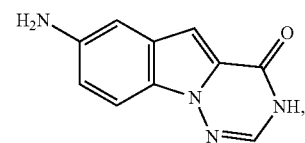

7-amino-[1,2,4]triazino[1,6-a]indol-4(3H)-one

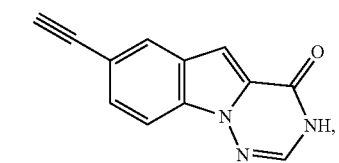

7-ethynyl-[1,2,4]triazino[1,6-a]indol-4(3H)-one

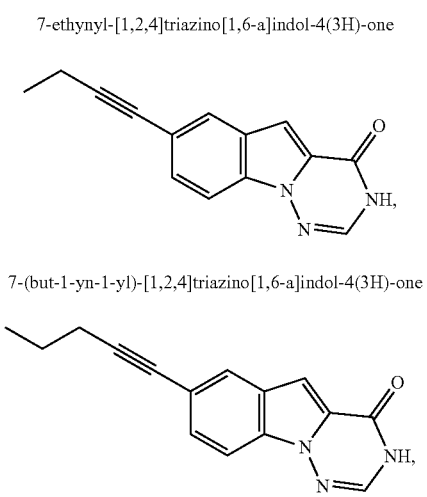

7-(but-1-yn-1-yl)-[1,2,4]triazino[1,6-a]indol-4(3H)-one

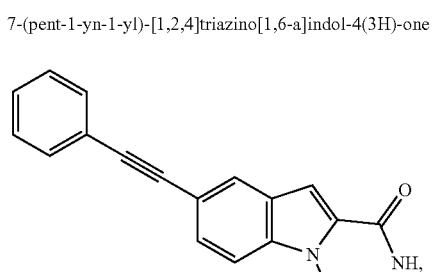

7-(pent-1-yn-1-yl)-[1,2,4]triazino[1,6-a]indol-4(3H)-one

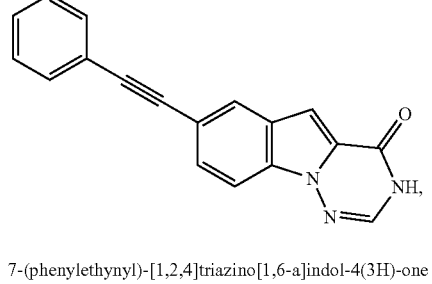

7-(phenylethynyl)-[1,2,4]triazino[1,6-a]indol-4(3H)-one

-continued

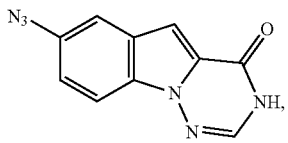

7-azido-[1,2,4]triazino[1,6-a]indol-4(3H)-one

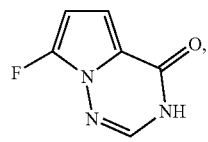

7-fluropyrrolo-[2,1-f][1,2,4]triazino-4(3H)-one

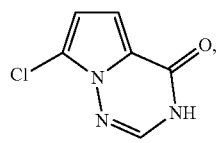

7-chloropyrrolo-[2,1-f][1,2,4]triazin-4(3H)-one

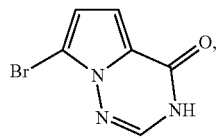

7-bromopyrrolo-[2,1-f][1,2,4]triazin-4(3H)-one

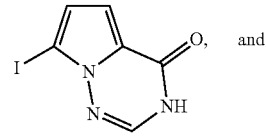

7-iodopyrrolo-[2,1-f][1,2,4]triazin-4(3H)-one

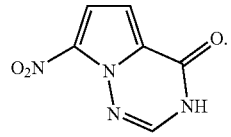

7-nitropyrrolo-[2,1-f][1,2,4]triazin-4(3H)-one

In another embodiment of the present invention triazine compounds of Formula II are useful for screening kinases and other related targets.

In an embodiment of the present invention a process for the preparation of triazine compounds of Formula II, said process comprising the steps of:

(a) stirring compounds of Formula I with sodium hypochlorite, Methyl tertiary-butyl ether (MTBE), methyltrioctylammonium chloride (aliquat-336), aqueous NaOH, ammonium chloride and aqueous NH$_4$OH at a temperature ranging between 25° C. to 35° C. for a period ranging between 2-4 hrs to obtain N-aminated substituted 2-carboxylate;

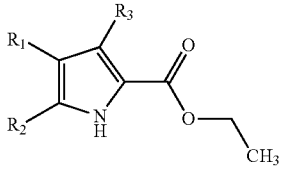

Formula-I wherein R1, R2, and R3, are independently selected from the group consisting of hydrogen, (C1-C6) alkyl, —NO$_2$, I, Cl, Br, F, and —CH$_2$—R7, where R7 is 5 or 6 membered saturated heterocyclic ring, comprising at least one heteroatom selected from the group consisting of N, O, and S which is directly attached to carbon atom of —CH$_2$; or R1 and R2 together form substituted or unsubstituted aromatic ring as set forth below:

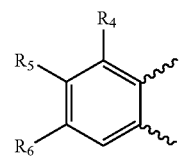

wherein R4, R5, and R6 are individually selected from the group consisting of hydrogen, (C1-C6) alkyl, —NH$_2$, halogen, —OH, —CN, —NO$_2$, aryl, alkylaryl, (C1-C8) alkoxy, aryloxy, arylalkoxy, N$_3$, and R—C≡C, where R is selected from the group consisting of hydrogen, (C1-C6)alkyl, aryl, and alkylaryl (b) heating the N-aminated substituted 2-carboxylate compounds as obtained in step (a) with formamide and ammonium acetate at 130° C. to 140° C. for a period ranging between 10 to 12 hr under nitrogen atmosphere to obtain triazine compounds of Formula II.

In another embodiment of the present invention compounds of Formula I used in step (a) are selected from the group consisting of:
ethyl 1H-pyrrole-2-carboxylate (5),
ethyl 3,5-dimethyl-1H-pyrrole-2-carboxylate (6),
ethyl 4-nitro-1H-pyrrole-2-carboxylate (7),
ethyl 5-methyl-1H-pyrrole-2-carboxylate (8),
ethyl 1H-indole-2-carboxylate (1),
ethyl 5-methoxy-1H-indole-2-carboxylate (9),
ethyl 5,6-dimethoxy-1H-indole-2-carboxylate (10),
ethyl 5-(benzyloxy)-1H-indole-2-carboxylate (11),
ethyl 5-cyano-1H-indole-2-carboxylate (12),
ethyl 5-fluoro-1H-indole-2-carboxylate (13),
ethyl 5-chloro-1H-indole-2-carboxylate (14),
ethyl 5-bromo-1H-indole-2-carboxylate (15),
ethyl 5-iodo-1H-indole-2-carboxylate (16),
ethyl 5-hydroxy-1H-indole-2-carboxylate (17),
ethyl 4-fluoro-1H-indole-2-carboxylate (18),
ethyl 4-chloro-1H-indole-2-carboxylate (19),
ethyl 4-bromo-1H-indole-2-carboxylate (20),
ethyl 4-iodo-1H-indole-2-carboxylate (21),
ethyl 4-hydroxy-1H-indole-2-carboxylate (22),
ethyl 5-nitro-1H-indole-2-carboxylate (23),
ethyl 3-(morpholinomethyl)-1H-indole-2-carboxylate (24),
ethyl 3-(pyrrolidin-1-ylmethyl)-1H-indole-2-carboxylate (25),
ethyl 5-amino-1H-indole-2-carboxylate (26), ethyl 5-ethynyl-1H-indole-2-carboxylate (27),
ethyl 5-(prop-1-yn-1-yl)-1H-indole-2-carboxylate (28),
ethyl 5-(but-1-yn-1-yl)-1H-indole-2-carboxylate (29),
ethyl 5-(phenylethynyl)-1H-indole-2-carboxylate (30),
ethyl 5-azido-1H-indole-2-carboxylate (31),
ethyl 5-fluoro-1H-pyrrole-2-carboxylate (32),
ethyl 5-chloro-1H-pyrrole-2-carboxylate (33),
ethyl 5-bromo-1H-pyrrole-2-carboxylate (34),
ethyl 5-iodo-1H-pyrrole-2-carboxylate (35),
ethyl 5-nitro-1H-pyrrole-2-carboxylate (36).

In another embodiment of the present invention N-aminated substituted 2-carboxylate as obtained in step (a) is either N-aminated pyrrole substituted 2-carboxylate or N-aminated indole substituted 2-carboxylate.

In another embodiment of the present invention yield of triazine compounds of Formula II is in the range of 75 to 85%.

BRIEF DESCRIPTION OF ACCOMPANYING DRAWINGS

DETAILED DESCRIPTION OF THE INVENTION

Figure 1:
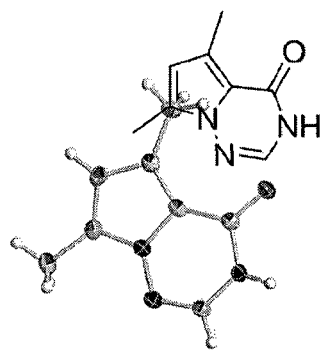
FIG. 1 depicts ORTEP diagram of the compound 38.
Figure 2:
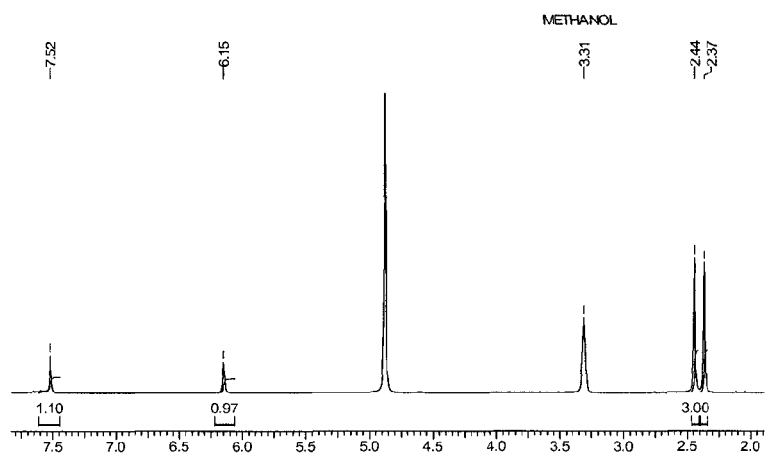
FIG. 2 depicts $^1$H NMR (CD$_3$OD, 200 MHz) spectrum of 5,7-dimethylpyrrolo[2,1-f][1,2,4]triazin-4(3H)-one.
Figure 3:
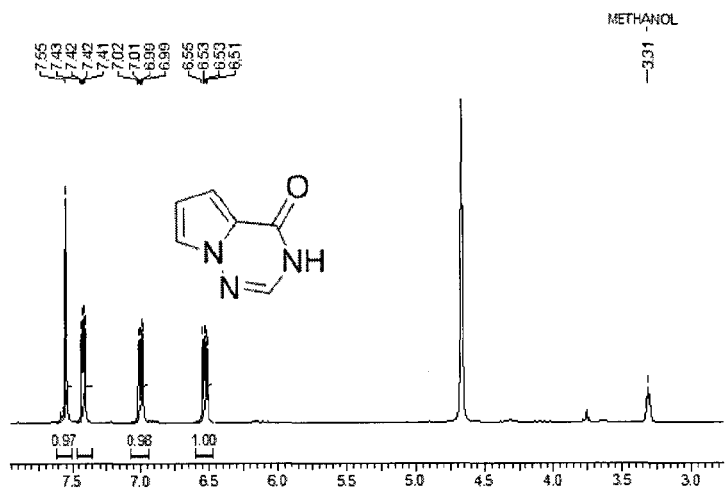
FIG. 3 depicts $^1$H NMR (CD$_3$OD, 500 MHz) spectrum of pyrrolo[2,1-f][1,2,4]triazin-4(3H)-one.
Figure 4:
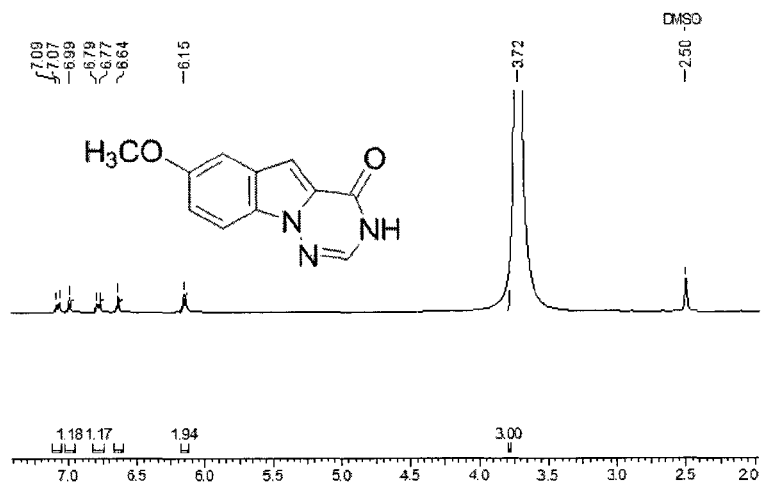
FIG. 4 depicts $^1$H NMR (DMSO-d$_6$, 500 MHz) spectrum of 7-methoxy-[1,2,4]triazino[1,6-a]indol-4(3H)-one.
Figure 5:
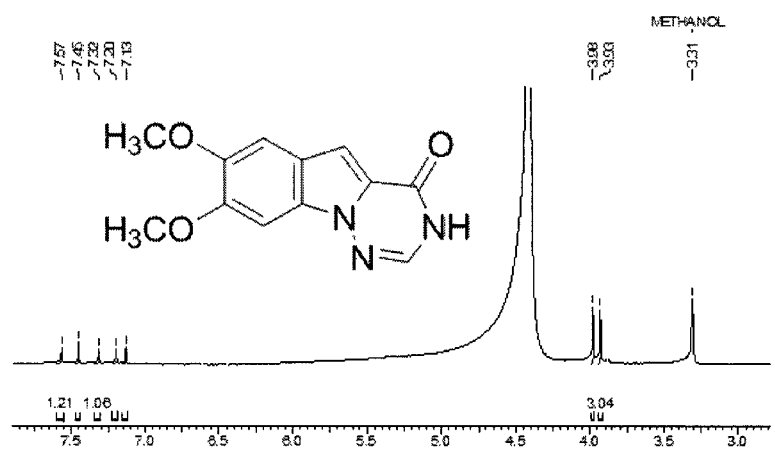
FIG. 5 depicts $^1$H NMR (CD$_3$OD, 400 MHz) spectrum of 7,8-dimethoxy-[1,2,4]triazino[1,6-a]indol-4(3H)-one.
Figure 6:
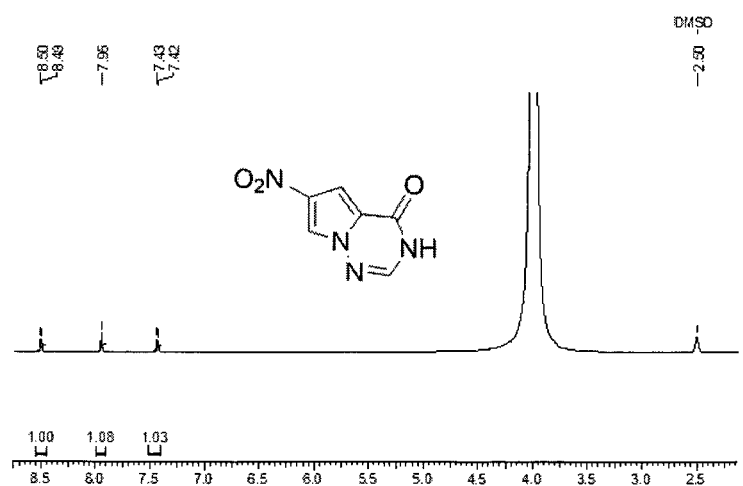
FIG. 6 depicts $^1$H NMR (DMSO-d$_6$, 400 MHz) spectrum of 6-nitropyrrolo[2,1-f][1,2,4]triazin-4(3H)-one.
Figure 7:
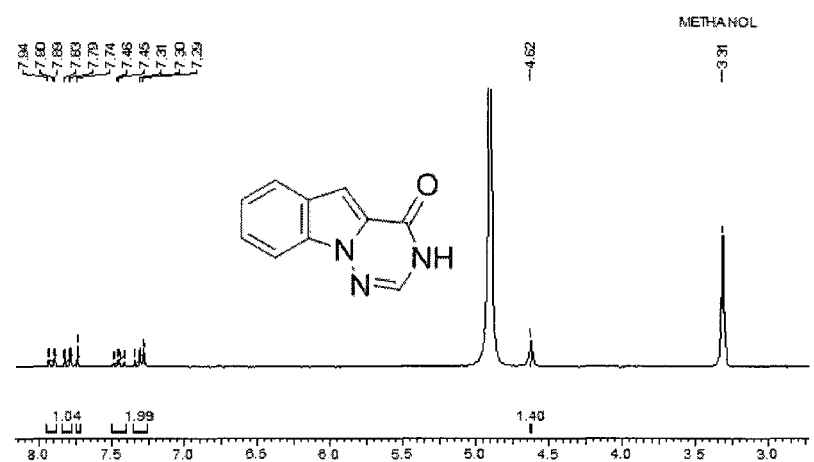
FIG. 7 depicts $^1$H NMR (CD$_3$OD, 400 MHz) spectrum of [1,2,4]triazino[1,6-a]indol-4(3H)-one.

The instant invention discloses triazine compounds and a short method to synthesize triazines nucleus, wherein the method comprises amination followed by Leuckart reaction conditions of pyrrole/indole-2-carboxylates of Formula I to obtain corresponding [1,2,4]triazine compounds of Formula II.

The instant invention thus provides short and efficient route for synthesis of various fused nitrogen ring system derivatives selected from a number of pyrrole and indole triazines. The synthesis of pyrrole triazinones and indole triazinones according to the invention has been accomplished in the instant invention using Leuckart reaction conditions.

The invention provides one pot method for synthesis of pyrrole/indole[1,2,4]triazine compounds of Formula II comprising steps of;

(a) subjecting pyrrole/indole-2-carboxylate compounds of Formula I to amination in presence of chloramine to obtain desired N-aminated pyrrole/indole-2-carboxylate in high yields;

(b) adding the N-aminated pyrrole/indole-2-carboxylate compound obtained from step (a) to formamide and ammonium acetate under Leuckart conditions to obtain pyrrole/indole[1,2,4]triazine compounds of Formula II.

N-Amination of various commercially available pyrrole-2-carboxylates and indole-2-carboxylates of Formula I is carried out using mono chloramine. N-amino pyrrole-2-carboxylate and N-amino-indole-2-carboxylates thus obtained were heated overnight at 140° C. under nitrogen atmosphere in formamide and ammonium acetate to give various pyrrole and indole triazine compounds of Formula II. The instant invention is schematically represented below in scheme 1.

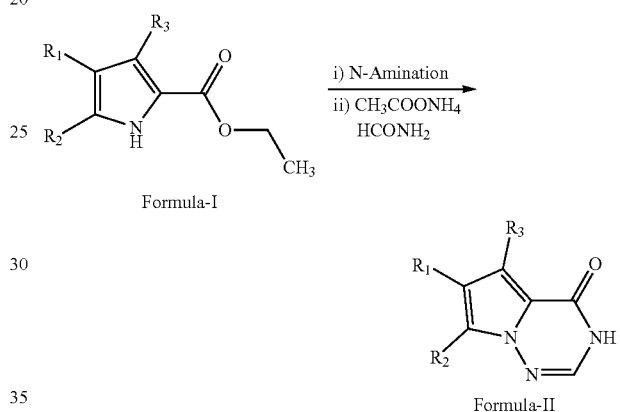

Scheme 1

Formula-I

Formula-II wherein, R1, R2 and R3, are independently selected from the group consisting of hydrogen, (C1-C6) alkyl, —NO$_2$, I, Cl, Br, F or —CH$_2$—R7, where R7 is 5 or 6 membered saturated heterocyclic ring, comprising at least one heteroatom selected from the group consisting of N, O, S which is directly attached to carbon atom of —CH$_2$ or R1 and R2 together form substituted or unsubstituted aromatic ring as follow;

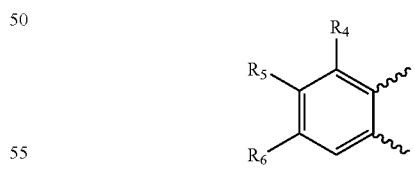

wherein R4, R5 and R6 is individually selected from the group consisting of hydrogen, (C1-C6) alkyl, —NH$_2$, halogen, —OH, —CN, —NO$_2$, aryl, alkylaryl, (C1-C8) alkoxy, aryloxy, arylalkoxy, N$_3$, R—C≡C—, where R is hydrogen, (C1-C6)alkyl, aryl, alkylaryl.

The proposed mechanism for cyclization using Leuckart condition according to the invention is shown below in scheme 2:

Scheme 2

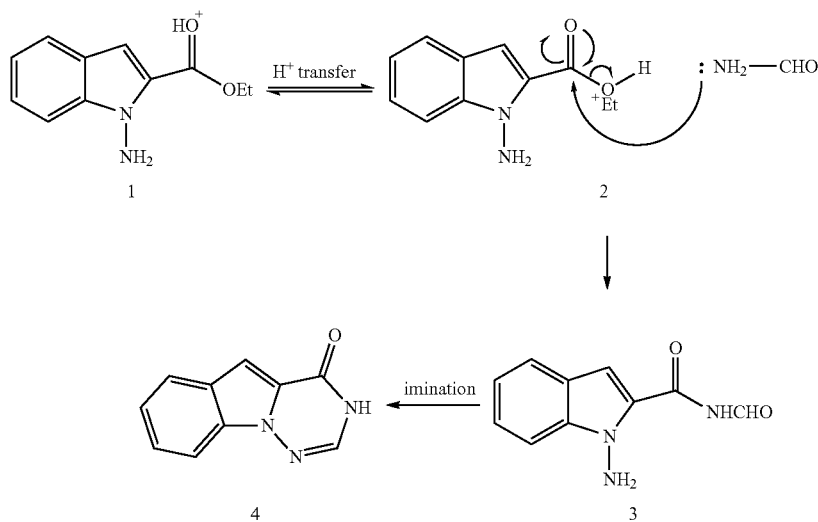

According to preferred aspect, N-aminated ethyl 3,5-dimethyl-1H-pyrrole-2-carboxylate (6) is prepared by adding aqueous sodium hypochlorite at room temperature to a vigorously stirred mixture of ethyl 3,5-dimethyl-1H-pyrrole-2-carboxylate in Methyl tertiary-butyl ether (MTBE), ammonium chloride, methyltrioctylammonium chloride (Aliquat-336), aqueous NaOH and aqueous NH$_4$OH. The resulting reaction mixture was stirred at room temperature for an additional 2-4 h at the end of which, the complete disappearance of starting material and formation of product is observed by capillary GC and HPLC. The upper product-rich organic layer was separated from the spent aqueous layer and washed with aqueous Na$_2$S$_2$O$_3$. The organic layer is then dried over anhydrous Na$_2$SO$_4$ and evaporated in vacuo to produce N-aminated ethyl 3,5-dimethyl-1H-pyrrole-2-carboxylate (6). The N-amination of indole-2-carboxylate, pyrrole-2-carboxylate and their derivatives according to the invention has been achieved using chloramine, which is generated in the aqueous layer through oxidation of ammonia by NaOCl. At the same time, the substrate is deprotonated in the organic phase methyl tertiary-butyl ether (MTBE) with the addition of a small amount of methyltrioctylammonium chloride (Aliquat-336), which promptly reacts with the small portion of chloramines present in the organic layer, affording the desired N—NH$_2$ derivative in high yields.

In another preferred aspect, the solution of N-aminated ethyl 3,5-dimethyl-1H-pyrrole-2-carboxylate (6) in formamide is added to NH$_4$OAc under stirring. The resulting mixture is stirred for 12-14 h at reflux temperature. The reaction mixture is poured into cold water and further diluted with ethyl acetate. The layers are separated and the aqueous layer is repeatedly extracted with ethyl acetate and the combined organic layers are dried over Na$_2$SO$_4$, filtered, and concentrated. The solvents are removed under reduced pressure to give the crude product mixture as colorless solid. Silica gel column chromatography of the crude product using petroleum ether/EtOAc (3:1) as eluent gave (38) as a colorless crystalline solid.

The $^1$H NMR spectrum of 1 clearly indicated broad singlet for —NH$_2$ at δ 4.68. Derivatives of N-amino pyrrole-2-carboxylate and N-amino-indole-2-carboxylates were heated overnight at 140° C. under nitrogen atmosphere in formamide and ammonium acetate to give cyclized pyrrole and indoletriazines.

In the present invention, various pyrroletriazinones and indoletriazinones have been accomplished using Leuckart reaction conditions from N-aminated precursors of pyrrole-2-carboxylate and N-amino-indole-2-carboxylates as depicted in table 1.

TABLE 1

One-pot synthesis of [1,2,4]triazino[1,6-a]indol-4(3H)-one and [1,2,4]riazino[1,6-a]pyrrole-4(3H)-one compounds

| Entry No. | N-Amination precursors | Products | Yields |
|---|---|---|---|
| 1. | 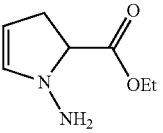 | 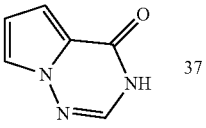 | 83% |

TABLE 1-continued
One-pot synthesis of [1,2,4]triazino[1,6-a]indol-4(3H)-one and
[1,2,4]triazino[1,6-a]pyrrole-4(3H)-one compounds
| Entry No. | N-Amination precursors | Products | Yields |
|---|---|---|---|
| 2. | 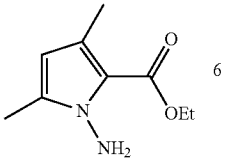 6 | 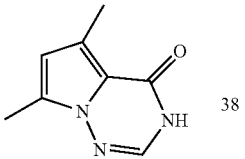 38 | 84% |
| 3. | 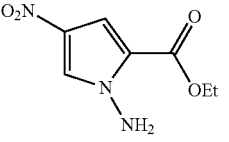 7 | 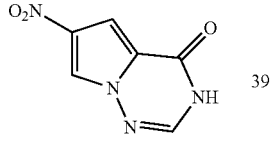 [SMILES: O=c1[nH]cnn2cc([N+](=O)[O-])cc12] 39 | 78% |
| 4. | 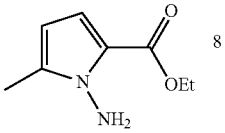 8 | 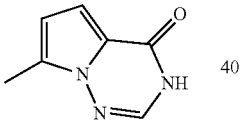 40 | 81% |
| 5. | 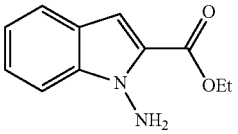 1 | 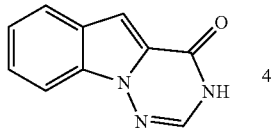 [SMILES: O=c1[nH]cnn2c1cc1ccccc12] 4 | 85% |
| 6. | 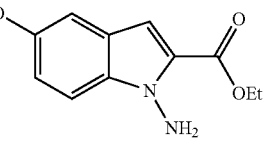 9 | 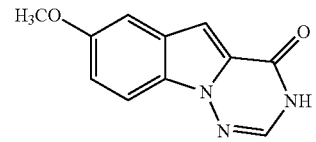 41 | 73% |
| 7. | 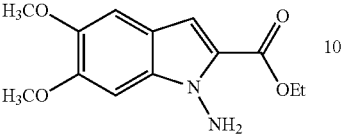 [SMILES: CCOC(=O)c1cc2cc(OC)c(OC)cc2n1N] 10 | 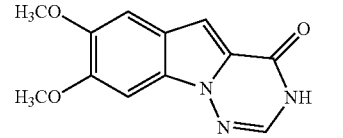 42 | 67% |
| 8. | 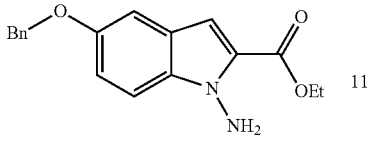 11 | 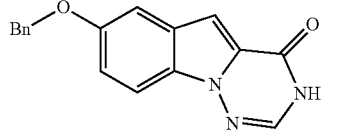 43 | — |
| 9. | 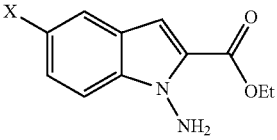 12, X = CN 13, X = F, 14, X = Cl, 15, X = Br, 16, X = I 17, X = OH | 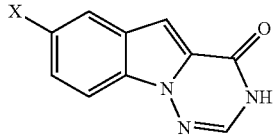 44, X = CN 45, X = F, 46, X = Cl, 47, X = Br, 48, X = I 49, X = OH | — |

TABLE 1-continued
One-pot synthesis of [1,2,4]triazino[1,6-a]indol-4(3H)-one and [1,2,4]riazino[1,6-a]pyrrole-4(3H)-one compounds
| Entry No. | N-Amination precursors | Products | Yields |
|---|---|---|---|
| 10. | 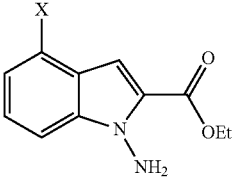<br>18, X = F<br>19, X = Cl<br>20, X = Br<br>21, X = I<br>22, X = OH | 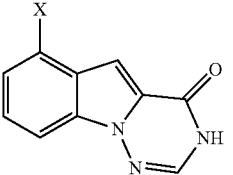<br>50, X = F<br>51, X = Cl<br>52, X = Br<br>53, X = I<br>54, X = OH | — |
| 11. | 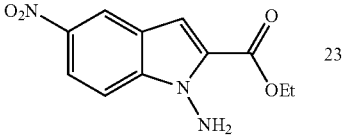 [SMILES: CCOC(=O)c1cc2cc([N+](=O)[O-])ccc2n1N] 23 | 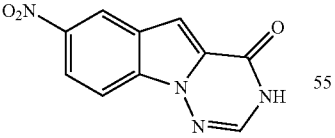 [SMILES: O=c1[nH]cnn2c1cc1cc([N+](=O)[O-])ccc12] 55 | — |
| 12. | 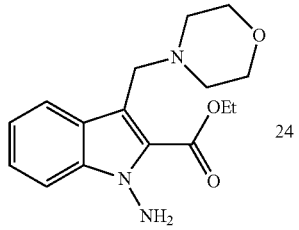 [SMILES: CCOC(=O)c1c(CN2CCOCC2)c2ccccc2n1N] 24 | 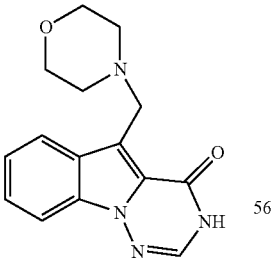 [SMILES: O=c1[nH]cnn2c1c(CN1CCOCC1)c1ccccc12] 56 | — |
| 13. | 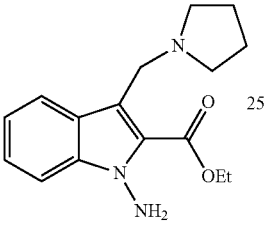 [SMILES: CCOC(=O)c1c(CN2CCCC2)c2ccccc2n1N] 25 | 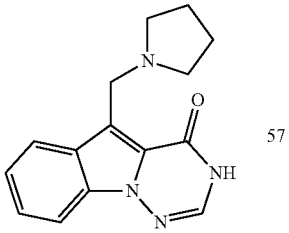 [SMILES: O=c1[nH]cnn2c1c(CN1CCCC1)c1ccccc12] 57 | — |
| 14. | 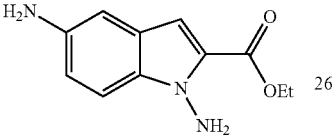 26 | 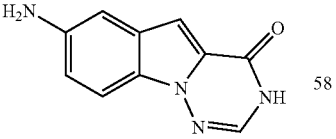 58 | — |
| 15. | 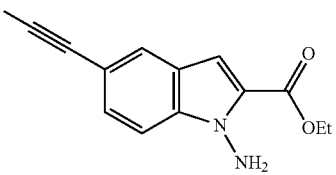<br>27, R = H,<br>28, R = Me<br>29, R = Et<br>30, R = Ph | 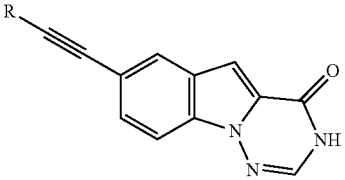<br>59, R = H,<br>60, R = Me<br>61, R = Et<br>62, R = Ph | — |

TABLE 1-continued

One-pot synthesis of [1,2,4]triazino[1,6-a]indol-4(3H)-one and
[1,2,4]riazino[1,6-a]pyrrole-4(3H)-one compounds

| Entry No. | N-Amination precursors | Products | Yields |
|---|---|---|---|
| 16. | 31 | 63 | — |
| 17. | 32, X = F<br>33, X = Cl<br>34, X = Br<br>35, X = I<br>36, X = NO$_2$ | 64, X = F<br>65, X = Cl<br>66, X = Br<br>67, X = I<br>68, X = NO$_2$ | |

The compounds of Formula II were synthesized according to invention encompasses triazine compounds as depicted in Table 2.

TABLE 2

IUPAC names of the compounds synthesized

| S. No. | Compound No. | I.U.P.A.C Names |
|---|---|---|
| i. | 37 | pyrrolo[2,1-f][1,2,4]triazin-4(3H)-one |
| ii. | 38 | 5,7-dimethylpyrrolo[2,1-f][1,2,4]triazin-4(3H)-one |
| iii. | 39 | 6-nitropyrrolo[2,1-f][1,2,4]triazin-4(3H)-one |
| iv. | 40 | 7-methylpyrrolo[2,1-f][1,2,4]triazin-4(3H)-one |
| v. | 04 | [1,2,4]triazino[1,6-a]indol-4(3H)-one |
| vi. | 41 | 7-methoxy-[1,2,4]triazino[1,6-a]indol-4(3H)-one |
| vii. | 42 | 7,8-dimethoxy-[1,2,4]triazino[1,6-a]indol-4(3H)-one |
| viii. | 43 | 7-(benzyloxy)-[1,2,4]triazino[1,6-a]indol-4(3H)-one |
| ix. | 44 | 4-oxo-3,4-dihydro-[1,2,4]triazino[1,6-a]indole-7-carbonitrile |
| x. | 45 | 7-fluoro-[1,2,4]triazino[1,6-a]indol-4(3H)-one |
| xi. | 46 | 7-chloro-[1,2,4]triazino[1,6-a]indol-4(3H)-one |
| xii. | 47 | 7-bromo-[1,2,4]triazino[1,6-a]indol-4(3H)-one |
| xiii. | 48 | 7-iodo-[1,2,4]triazino[1,6-a]indol-4(3H)-one |
| xiv. | 49 | 7-hydroxy-[1,2,4]triazino[1,6-a]indol-4(3H)-one |
| xv. | 50 | 6-fluoro-[1,2,4]triazino[1,6-a]indol-4(3H)-one |
| xvi. | 51 | 6-chloro-[1,2,4]triazino[1,6-a]indol-4(3H)-one |
| xvii. | 52 | 6-bromo-[1,2,4]triazino[1,6-a]indol-4(3H)-one |
| xviii. | 53 | 6-iodo-[1,2,4]triazino[1,6-a]indol-4(3H)-one |
| xix. | 54 | 6-hydroxy-[1,2,4]triazino[1,6-a]indol-4(3H)-one |
| xx. | 55 | 7-nitro-[1,2,4]triazino[1,6-a]indol-4(3H)-one |
| xxi. | 56 | 5-(morpholinomethyl)-[1,2,4]triazino[1,6-a]indol-4(3H)-one |
| xxii. | 57 | 5-(pyrrolidin-1-ylmethyl)-[1,2,4]triazino[1,6-a]indol-4(3H)-one |
| xxiii. | 58 | 7-amino-[1,2,4]triazino[1,6-a]indol-4(3H)-one |
| xxiv. | 59 | 7-ethynyl-[1,2,4]triazino[1,6-a]indol-4(3H)-one |
| xxv. | 60 | 7-(but-1-yn-1-yl)-[1,2,4]triazino[1,6-a]indol-4(3H)-one |
| xxvi. | 61 | 7-(pent-1-yn-1-yl)-[1,2,4]triazino[1,6-a]indol-4(3H)-one |
| xxvii. | 62 | 7-(phenylethynyl)-[1,2,4]triazino[1,6-a]indol-4(3H)-one |
| xxviii. | 63 | 7-azido-[1,2,4]triazino[1,6-a]indol-4(3H)-one |
| xxix. | 64 | 7-fluoropyrrolo[2,1-f][1,2,4]triazin-4(3H)-one |
| xxx. | 65 | 7-chloropyrrolo[2,1-f][1,2,4]triazin-4(3H)-one |
| xxxi. | 66 | 7-bromopyrrolo[2,1-f][1,2,4]triazin-4(3H)-one |
| xxxii. | 67 | 7-iodopyrrolo[2,1-f][1,2,4]triazin-4(3H)-one |
| xxxiii. | 68 | 7-nitropyrrolo[2,1-f][1,2,4]triazin-4(3H)-one |

The N-aminated precursors as well as cyclized triazines are characterized by spectral data. The $^1$H NMR spectrum of compound 38 showed the presence of olefinic proton at δ 7.52 (s, 1H) and in $^{13}$C NMR spectrum of compound 38 showed the presence of amide carbonyl at 159.9 ppm. confirms the formation of [1,2,4]triazino[1,6-a]indol-4(3H)-one and [1,2,4]triazino[1,6-a]pyrrole-4(3H)-one. Further in order to confirm reaction product 38, recrystallisation was done by slow evaporation of the solution mixture of ethyl acetate and hexane to give the clear crystalline solid, which was analysed for single X-ray crystallography. The ORTEP diagram (FIG. 1) clearly established the formation of triazines.

The present invention encompasses novel triazine compounds of Formula II,

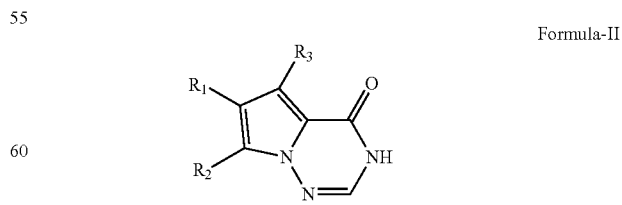

Formula-II wherein, R1, R2, and R3, are independently selected from the group consisting of hydrogen, (C1-C6) alkyl, —NO$_2$, I, Cl, Br, F, and —CH$_2$—R7, where R7 is 5 or 6 membered saturated heterocyclic ring, comprising at least one heteroatom selected from the group consisting of N, O, and S which is directly attached to carbon atom of —CH$_2$; or R1 and R2 together form substituted or unsubstituted aromatic ring as set forth below:

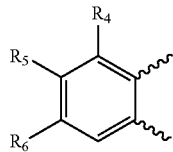

wherein R4, R5, and R6 are individually selected from the group consisting of hydrogen, (C1-C6) alkyl, —NH$_2$, halogen, —OH, —CN, —NO$_2$, aryl, alkylaryl, (C1-C8) alkoxy, aryloxy, arylalkoxy, N$_3$, and R—C≡C—, where R is selected from the group consisting of hydrogen, (C1-C6) alkyl, aryl, and alkylaryl.

According to the invention, the novel triazine compounds of Formula H, are selected from the group consisting of:

| Compound No. | I.U.P.A.C Names |
|---|---|
| 38 | 5,7-dimethylpyrrolo[2,1-f][1,2,4]triazin-4(3H)-one |
| 04 | [1,2,4]triazino[1,6-a]indol-4(3H)-one |
| 41 | 7-methoxy-[1,2,4]triazino[1,6-a]indol-4(3H)-one |
| 42 | 7,8-dimethoxy-[1,2,4]triazino[1,6-a]indol-4(3H)-one |
| 43 | 7-(benzyloxy)-[1,2,4]triazino[1,6-a]indol-4(3H)-one |
| 44 | 4-oxo-3,4-dihydro-[1,2,4]triazino[1,6-a]indole-7-carbonitrile |
| 45 | 7-fluoro-[1,2,4]triazino[1,6-a]indol-4(3H)-one |
| 46 | 7-chloro-[1,2,4]triazino[1,6-a]indol-4(3H)-one |
| 47 | 7-bromo-[1,2,4]triazino[1,6-a]indol-4(3H)-one |
| 48 | 7-iodo-[1,2,4]triazino[1,6-a]indol-4(3H)-one |
| 49 | 7-hydroxy-[1,2,4]triazino[1,6-a]indol-4(3H)-one |
| 50 | 6-fluoro-[1,2,4]triazino[1,6-a]indol-4(3H)-one |
| 51 | 6-chloro-[1,2,4]triazino[1,6-a]indol-4(3H)-one |
| 52 | 6-bromo-[1,2,4]triazino[1,6-a]indol-4(3H)-one |
| 53 | 6-iodo-[1,2,4]triazino[1,6-a]indol-4(3H)-one |
| 54 | 6-hydroxy-[1,2,4]triazino[1,6-a]indol-4(3H)-one |
| 55 | 7-nitro-[1,2,4]triazino[1,6-a]indol-4(3H)-one |
| 56 | 5-(morpholinomethyl)-[1,2,4]triazino[1,6-a]indol-4(3H)-one |
| 57 | 5-(pyrrolidin-1-ylmethyl)-[1,2,4]triazino[1,6-a]indol-4(3H)-one |
| 58 | 7-amino-[1,2,4]triazino[1,6-a]indol-4(3H)-one |
| 59 | 7-ethynyl-[1,2,4]triazino[1,6-a]indol-4(3H)-one |
| 60 | 7-(but-1-yn-1-yl)-[1,2,4]triazino[1,6-a]indol-4(3H)-one |
| 61 | 7-(pent-1-yn-1-yl)-[1,2,4]triazino[1,6-a]indol-4(3H)-one |
| 62 | 7-(phenylethynyl)-[1,2,4]triazino[1,6-a]indol-4(3H)-one |
| 63 | 7-azido-[1,2,4]triazino[1,6-a]indol-4(3H)-one |
| 64 | 7-fluoropyrrolo[2,1-f][1,2,4]triazin-4(3H)-one |
| 65 | 7-chloropyrrolo[2,1-f][1,2,4]triazin-4(3H)-one |
| 66 | 7-bromopyrrolo[2,1-f][1,2,4]triazin-4(3H)-one |
| 67 | 7-iodopyrrolo[2,1-f][1,2,4]triazin-4(3H)-one |
| 68 | 7-nitropyrrolo[2,1-f][1,2,4]triazin-4(3H)-one |

In another embodiment, the present invention provides a pharmaceutical composition comprising instant triazine compounds of Formula II or its pharmaceutically acceptable salts, along with pharmaceutically acceptable excipients or carriers, for the treatment of cancer in human. Further the composition may be formulated into preparations such as solid, semi-solid, liquid or gaseous forms, such as tablets, capsules, powders, granules, ointments, syrup, solutions, injections, gels and microspheres etc.

Generally, the quantity of active compound of Formula II ranges between 0.5% to 90% by weight of the composition. Normally, the effective amount of dosage of triazine compounds will be in the range of about 0.1 to about 100 mg/kg, more preferably about 1.0 mg to about 50 mg/kg of body weight/day.

The pharmaceutical compositions of the invention can be prepared by combining a compound of Formula II the invention with an appropriate pharmaceutically acceptable carrier, diluent or excipient. The excipients or carriers are selected from the group such as diluents, disintegrants, binders, lubricants, coatings layer, stabilizers, preservatives, glidants.

In another embodiment, the present invention relates to administering 'an effective amount' of the 'composition of invention' to the subject suffering from cancer. Typical routes of administering such pharmaceutical compositions include, oral, topical, transdermal, inhalation, parenteral, sublingual, buccal, rectal, vaginal, and intranasal.

The invention provides method of inhibiting tyrosine kinase comprises administering an effective amount of triazine compounds of Formula II or its pharmaceutical salt in association with one or more pharmaceutical carriers/excipients.

In another embodiment, the invention provides a method of treating or inhibiting growth of cancer cells in a subject comprising administrating triazine compounds of Formula II optionally comprising administering at least one additional active compound together with pharmaceutically acceptable excipients and/or vehicles, Further invention provides use of triazine compounds of Formula II for the preparation of medicament useful for treating or inhibiting the growth of cancer cells in a subject. The subject disclosed in the invention is human.

EXAMPLES

Following are the examples given to further illustrate the invention and should not be construed to limit the scope of the present invention.

Example 1

General Experimental Procedure for N-Amination Reaction

Aqueous sodium hypochlorite (58.76 ml of ca. 9% solution) was added over a period of 20 min, at room temperature (25° C.), to a vigorously stirred mixture of (3,4,5,6-substituted-1-H-pyrrole/indole-2-carboxylic acid ethyl ester) (2 g, 8.9 mmol) in MTBE (24 ml), ammonium chloride (2.9 g, 53.2 mmol), methyltrioctylammonium chloride (Aliquat-336) (0.1 g), aqueous NaOH (25.6 ml of 28.4% solution) and aqueous NH$_4$OH (8.28 ml of 28% solution). The resulting reaction mixture was stirred at room temperature for an additional 2-4 h at the end of which time the complete disappearance of starting material and formation of product was observed by capillary GC and HPLC. The upper product-rich organic layer was separated from the spent aqueous layer and washed with aqueous Na$_2$S$_2$O$_3$ (40 ml). The organic layer was then dried over anhydrous Na$_2$SO4 and evaporated in vacuo to produce 2.01 g of (1-amino-3,4,5,6-substituted-1-H-pyrrole/indole-2-carboxylic acid ethyl ester) (94% yield).

Example 2

General Experimental Procedure for Cyclization Reaction

To a stirring solution of (1-amino-3,4,5,6-substituted-1-H-pyrrole/indole-2-carboxylic acid ethyl ester) in formamide (5 ml) was added NH$_4$OAc. The resulting mixture was heated overnight at 140° C. under nitrogen atmosphere. The mixture was poured into cold water and further diluted with ethyl acetate. The layers were separated and the aqueous layer was extracted with ethyl acetate (2×20 mL). The combined organic layers were dried over $Na_2SO_4$, filtered, and concentrated. The solvents were removed under reduced pressure to give the crude product mixture as colorless solid. Silica gel column chromatography of the crude product using petroleum ether/EtOAc (3:1) as eluent gave (Pyrrolo/Indole[1,2,4]triazin-4(3H)-one) (83% yield) as a colorless crystalline solid.

Using the above procedure, the following cyclized triazines compounds have been prepared.

Example 3

5,7-dimethylpyrrolo[2,1-f][1,2,4]triazin-4(3H)-one (38)

| Name of Compound | Mol. Wt | mmoles | Equivalent | Density | Weight/volume |
|---|---|---|---|---|---|
| ethyl 1-amino-3,5-dimethyl-1H-pyrrole-2-carboxylate | 163.18 | 1.23 | 1 | | 200 mg |
| $NH_4OAc$ | 77.08 | 1.845 | 1.5 | | 142.21 mg |
| Time & Temp | 140° C. & 12 h | | | | |

Example 4 pyrrolo[2,1-f][1,2,4]triazin-4(3H)-one (37)

| Name of Compound | Mol. Wt | mmoles | Equivalent | Density | Weight/volume |
|---|---|---|---|---|---|
| ethyl 1-amino-1H-pyrrole-2-carboxylate | 135.12 | 1.48 | 1 | | 200 mg |
| $NH_4OAc$ | 77.08 | 2.22 | 1.5 | | 171.12 mg |
| Time & Temp | 140° C. & 12 h | | | | |

Example 5

7-methoxy-[1,2,4]triazino[1,6-a]indol-4(3H)-one (41)

| Name of Compound | Mol. Wt | mmoles | Equivalent | Density | Weight/volume |
|---|---|---|---|---|---|
| ethyl 1-amino-5-methoxy-1H-indole-2-carboxylate | 215.07 | 0.93 | 1 | | 200 mg |
| $NH_4OAc$ | 77.08 | 1.4 | 1.5 | | 107.53 mg |
| Time & Temp | 140° C. & 12 h | | | | |

Example 6

7,8-dimethoxy-[1,2,4]triazino[1,6-a]indol-4(3H)-one (42)

| Name of Comp. | Mol. Wt | mmoles | equivalent | density | Weight/volume |
|---|---|---|---|---|---|
| ethyl 1-amino-5,6-dimethoxy-1H-indole-2-carboxylate | 245.23 | 0.82 | 1 | | 200 mg |
| $NH_4OAc$ | 77.08 | 1.23 | 1.5 | | 94.80 mg |
| Time & Temp | 140° C. & 12 h | | | | |

Example 7

6-nitropyrrolo[2,1-f][1,2,4]triazin-4(3H)-one (39)

| Name of Compound | Mol. Wt | mmoles | Equivalent | Density | Weight/volume |
|---|---|---|---|---|---|
| ethyl 1-amino-4-nitro-1H-pyrrole-2-carboxylate | 180.12 | 1.11 | 1 | | 200 mg |
| $NH_4OAc$ | 77.08 | 1.67 | 1.5 | | 128.34 mg |
| Time & Temp | 140° C. & 12 h | | | | |

Example 8

[1,2,4]triazino[1,6-a]indol-4(3H)-one (04)

| Name of Compound | Mol. Wt | mmoles | Equivalent | Density | Weight/volume |
|---|---|---|---|---|---|
| ethyl 1-amino-1H-indole-2-carboxylate | 185.18 | 1.08 | 1 | | 200 mg |
| $NH_4OAc$ | 77.08 | 1.62 | 1.5 | | 124.87 mg |
| Time & Temp | 140° C. & 12 h | | | | |

ADVANTAGES OF INVENTION

The instant method is short and efficient for synthesis of various fused nitrogen ring system derivatives also the method avoids cumbersome intermediate steps and expensive solvents. Therefore, the instant invention is cost effective and industrially viable.

We claim:
1. A triazine compound of Formula II,

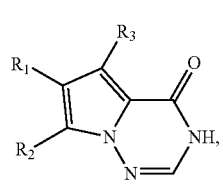

Formula-II wherein, R1 is selected from the group consisting of hydrogen, —NO₂, Br, F, and —CH₂—R7, where R7 is 5 or 6 membered saturated heterocyclic ring, comprising at least one heteroatom selected from the group consisting of N, O, and S which is directly attached to carbon atom of —CH₂; and wherein R2 is selected from the group consisting of —NO₂, I, Cl, F, and —CH₂—R7, wherein R7 is a 5 or 6 membered saturated heterocyclic ring, comprising at least one heteroatom selected from the group consisting of N, O, and S, which is directly attached to carbon atom of —CH₂; and wherein R3 is selected from the group consisting of hydrogen, —NO₂, I, F, and —CH₂—R7, wherein R7 is a 5 or 6 membered saturated heterocyclic ring, comprising at least one heteroatom selected from the group consisting of N, O, and S, which is directly attached to carbon atom of —CH₂; or R1 and R2 together form substituted or unsubstituted aromatic ring as set forth below:

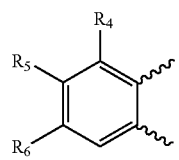

wherein R4, R5, and R6 are individually selected from the group consisting of hydrogen, (C1-C6) alkyl, —NH₂, halogen, —OH, —CN, —NO₂, aryl, alkylaryl, (C1-C8) alkoxy, aryloxy, arylalkoxy, N₃, and R—C≡C—, where R is selected from the group consisting of hydrogen, (C1-C6)alkyl, aryl, and alkylaryl.

2. The triazine compound as claimed in claim 1, wherein the structural formula of the representative compound is selected from the group consisting of:

4

(04)

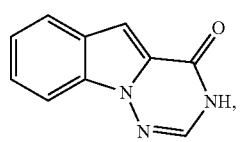

[1,2,4]triazino[1,6-a]indol-4(3H)-one

41

(41)

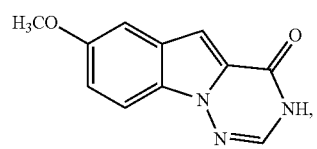

7-methoxy-[1,2,4]triazino[1,6-a]indol-4(3H)-one (42)

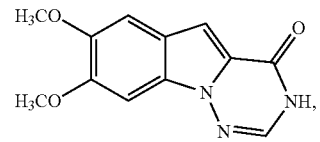

7-8-dimethoxy-[1,2,4]triazino[1,6-a]indol-4(3H)-one (43)

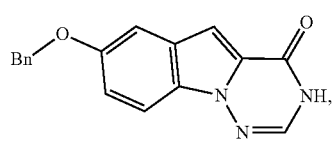

7-(benzyloxy)-[1,2,4]triazino[1,6-a]indol-4(3H)-one (44)

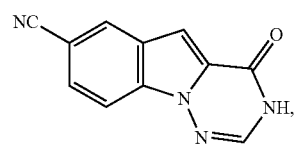

4-oxo-3,4-dihydro-[1,2,4]triazino[1,6-a]indole-7-carbonitrile (45)

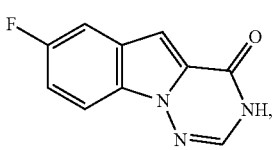

7-fluoro-[1,2,4]triazino[1,6-a]indol-4(3H)-one (46)

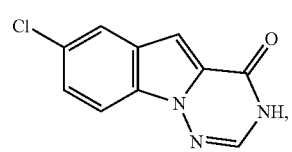

7-chloro-[1,2,4]triazino[1,6-a]indol-4(3H)-one (47)

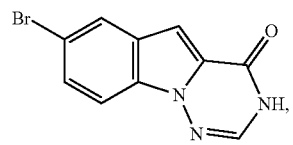

7-bromo-[1,2,4]triazino[1,6-a]indol-4(3H)-one (48)

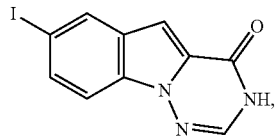

7-iodo-[1,2,4]triazino[1,6-a]indol-4(3H)-one

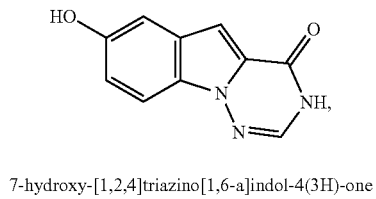

7-hydroxy-[1,2,4]triazino[1,6-a]indol-4(3H)-one (49)

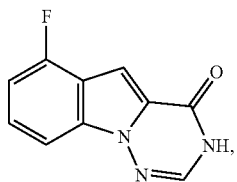

6-fluoro-[1,2,4]triazino[1,6-a]indol-4(3H)-one (50)

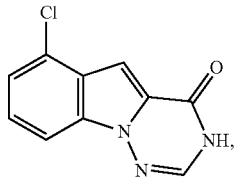

6-chloro-[1,2,4]triazino[1,6-a]indol-4(3H)-one (51)

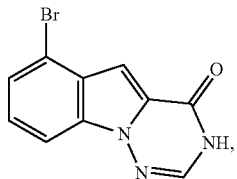

6-bromo-[1,2,4]triazino[1,6-a]indol-4(3H)-one (52)

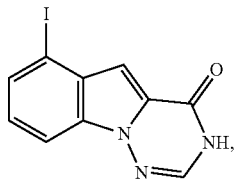

6-iodo-[1,2,4]triazino[1,6-a]indol-4(3H)-one (53)

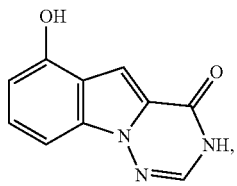

6-hydroxy-[1,2,4]triazino[1,6-a]indol-4(3H)-one (54)

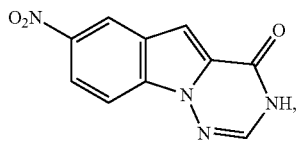

7-nitro-[1,2,4]triazino[1,6-a]indol-4(3H)-one (55)

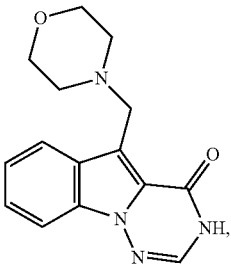

5-(morpholinomethyl)-[1,2,4]triazino[1,6-a]indol-4(3H)-one (56)

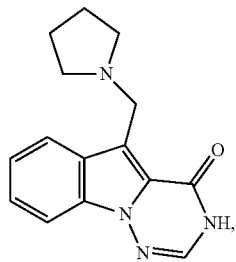

5-(pyrrolidin-1-ylmethyl)-[1,2,4]triazino[1,6-a]indol-4(3H)-one (57)

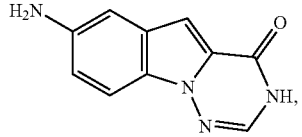

7-amino-[1,2,4]triazino[1,6-a]indol-4(3H)-one (58)

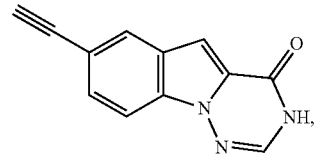

7-ethynyl-[1,2,4]triazino[1,6-a]indol-4(3H)-one (59)

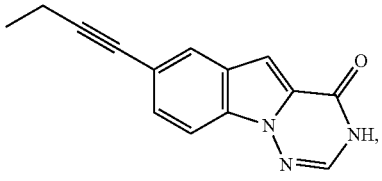

7-(but-1-yn-1-yl)-[1,2,4]triazino[1,6-a]indol-4(3H)-one (60)

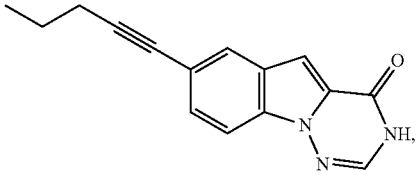

7-(pent-1-yn-1-yl)-[1,2,4]triazino[1,6-a]indol-4(3H)-one (61)

-continued (62)

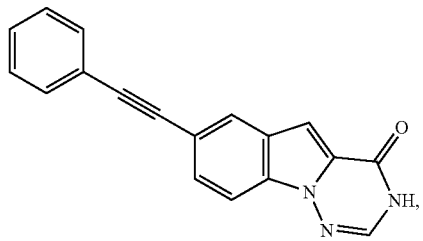

7-(phenylethynyl)-[1,2,4]triazino[1,6-a]indol-4(3H)-one (63)

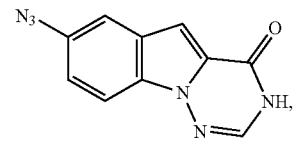

7-azido-[1,2,4]triazino[1,6-a]indol-4(3H)-one (64)

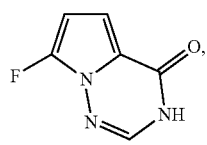

7-fluropyrrolo-[2,1-f][1,2,4]triazino-4(3H)-one (65)

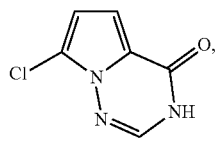

7-chloropyrrolo-[2,1-f][1,2,4]triazin-4(3H)-one (67)

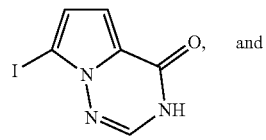

7-iodopyrrolo-[2,1-f][1,2,4]triazin-4(3H)-one (68)

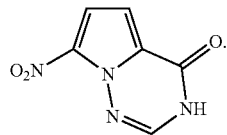

7-nitropyrrolo-[2,1-f][1,2,4]triazin-4(3H)-one

3. A process for the preparation of triazine compound of Formula II as claimed in claim 1, said process comprising the steps of:
(a) stirring compound of Formula I with sodium hypochlorite, Methyl tertiary-butyl ether (MTBE), methyltrioctylammonium chloride (aliquat-336), aqueous NaOH, ammonium chloride and aqueous NH₄OH at a temperature ranging between 25° C. to 35° C. for a period ranging between 2-4 hrs to obtain N-aminated substituted 2-carboxylate;

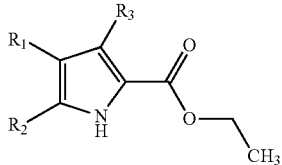

Formula-I wherein, R1 is selected from the group consisting of hydrogen, —NO₂, Br, F, and —CH₂—R7, where R7 is 5 or 6 membered saturated heterocyclic ring, comprising at least one heteroatom selected from the group consisting of N, O, and S which is directly attached to carbon atom of —CH₂; and wherein R2 is selected from the group consisting of —NO₂, I, Cl, F, and —CH₂—R7, wherein R7 is a 5 or 6 membered saturated heterocyclic ring, comprising at least one heteroatom selected from the group consisting of N, O, and S, which is directly attached to carbon atom of —CH₂; and wherein R3 is selected from the group consisting of hydrogen, —NO₂, I, F, and —CH₂—R7 wherein R7 is a 5 or 6 membered saturated heterocyclic ring, comprising at least one heteroatom selected from the group consisting of N, O, and S, which is directly attached to carbon atom of —CH₂; or R1 and R2 together form substituted or unsubstituted aromatic ring as set forth below:

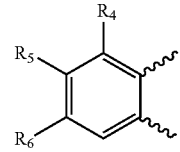

wherein R4, R5, and R6 are individually selected from the group consisting of hydrogen, (C1-C6) alkyl, —NH₂, halogen, —OH, —CN, —NO₂, aryl, alkylaryl, (C1-C8) alkoxy, aryloxy, arylalkoxy, N₃, and R—C≡C, where R is selected from the group consisting of hydrogen, (C1-C6)alkyl, aryl, and alkylaryl (b) heating the N-aminated substituted 2-carboxylate compounds as obtained in step (a) with formamide and ammonium acetate at 130° C. to 140° C. for a period ranging between 10 to 12 hr under nitrogen atmosphere to obtain triazine compound of Formula II.

4. The process as claimed in claim 3, wherein the compound of Formula I is selected from the group consisting of:
ethyl 1H-pyrrole-2-carboxylate (5),
ethyl 3,5-dimethyl-1H-pyrrole-2-carboxylate (6),
ethyl 4-nitro-1H-pyrrole-2-carboxylate (7),
ethyl 5-methyl-1H-pyrrole-2-carboxylate (8),
ethyl 1H-indole-2-carboxylate (1),
ethyl 5-methoxy-1H-indole-2-carboxylate (9),
ethyl 5,6-dimethoxy-1H-indole-2-carboxylate (10),
ethyl 5-(benzyloxy)-1H-indole-2-carboxylate (11),
ethyl 5-cyano-1H-indole-2-carboxylate (12),
ethyl 5-fluoro-1H-indole-2-carboxylate (13),
ethyl 5-chloro-1H-indole-2-carboxylate (14),
ethyl 5-bromo-1H-indole-2-carboxylate (15),
ethyl 5-iodo-1H-indole-2-carboxylate (16),
ethyl 5-hydroxy-1H-indole-2-carboxylate (17), ethyl 4-fluoro-1H-indole-2-carboxylate (18),
ethyl 4-chloro-1H-indole-2-carboxylate (19),
ethyl 4-bromo-1H-indole-2-carboxylate (20),
ethyl 4-iodo-1H-indole-2-carboxylate (21),
ethyl 4-hydroxy-1H-indole-2-carboxylate (22),
ethyl 5-nitro-1H-indole-2-carboxylate (23),
ethyl 3-(morpholinomethyl)-1H-indole-2-carboxylate, (24),
ethyl 3-(pyrrolidin-1-ylmethyl)-1H-indole-2-carboxylate (25),
ethyl 5-amino-1H-indole-2-carboxylate (26),
ethyl 5-ethynyl-1H-indole-2-carboxylate (27),
ethyl 5-(prop-1-yn-1-yl)-1H-indole-2-carboxylate (28),
ethyl 5-(but-1-yn-1-yl)-1H-indole-2-carboxylate (29),
ethyl 5-(phenylethynyl)-1H-indole-2-carboxylate (30),
ethyl 5-azido-1H-indole-2-carboxylate (31),
ethyl 5-fluoro-1H-pyrrole-2-carboxylate (32),
ethyl 5-chloro-1H-pyrrole-2-carboxylate (33),
ethyl 5-bromo-1H-pyrrole-2-carboxylate (34),
ethyl 5-iodo-1H-pyrrole-2-carboxylate (35), and
ethyl 5-nitro-1H-pyrrole-2-carboxylate (36).

5. The process as claimed in claim 3, wherein N-aminated substituted 2-carboxylate as obtained in step (a) is either N-aminated pyrrole substituted 2-carboxylate or N-aminated indole substituted 2-carboxylate.

6. The process as claimed in claim 3, wherein yield of triazine compound of Formula II is in the range of 75 to 85%.

* * * * *